United States Patent
AlJabri et al.

(10) Patent No.: US 11,427,742 B2
(45) Date of Patent: Aug. 30, 2022

(54) FLUORESCENT DYE LOADED POLYMERIC TAGGANTS FOR DEPTH DETERMINATION IN DRILLING WELLS

(71) Applicant: Saudi Arabian Oil Company, Dhahran (SA)

(72) Inventors: Nouf AlJabri, Dhahran (SA); Alberto F. Marsala, Dhahran (SA); Shitong Sherry Zhu, Cambridge, MA (US); Marta Antoniv, Cambridge, MA (US)

(73) Assignee: Saudi Arabian Oil Company, Dhahran (SA)

( * ) Notice: Subject to any disclaimer, the term of this patent is extended or adjusted under 35 U.S.C. 154(b) by 257 days.

(21) Appl. No.: 17/001,467

(22) Filed: Aug. 24, 2020

(65) Prior Publication Data
US 2022/0056329 A1   Feb. 24, 2022

(51) Int. Cl.
*C09K 8/035* (2006.01)
*C09K 11/02* (2006.01)
(Continued)

(52) U.S. Cl.
CPC .............. *C09K 8/035* (2013.01); *C09K 11/02* (2013.01); *C09K 11/06* (2013.01); *E21B 21/08* (2013.01);
(Continued)

(58) Field of Classification Search
CPC ........ C09K 8/035; C09K 11/02; C09K 11/06; C09K 2208/10; C09K 2211/1007;
(Continued)

(56) References Cited

U.S. PATENT DOCUMENTS 7,937,222 B2   5/2011   Donadille et al.
8,627,902 B2   1/2014   Hammer
(Continued)

FOREIGN PATENT DOCUMENTS

CA   2851237   5/2013
GB   2489714   10/2012
(Continued)

OTHER PUBLICATIONS

Allard et al., "Core-shell type dually fluorescent polymer nanoparticles for ratiometric pH-sensing," J. Polym. Sci., Part A: Polym. Chem., 2008, 46(18):6206-6213.
(Continued)

*Primary Examiner* — Mark R Gaworecki
(74) *Attorney, Agent, or Firm* — Fish & Richardson P.C.

(57) ABSTRACT

A method of surface logging a well includes adding each of multiple polymeric taggants to a circulating drilling fluid in an addition sequence while drilling the well. Each polymeric taggant includes a polymer and a respective fluorescent dye having an emission wavelength or excitation wavelength different from that of each other fluorescent dye. The method includes taking a sample of drill cuttings carried by a drilling fluid while drilling a well, wherein the sample of drill cuttings includes polymeric taggants attached to the drill cuttings. The method includes extracting the dyes from the sample of drill cuttings into an extract solution; determining an indication of the type of and the concentration of each of the dyes in the extract solution; and determining a depth associated with the sample of drill cuttings based on the indication of the concentration of each of the dyes and on the addition sequence.

28 Claims, 14 Drawing Sheets

US 11,427,742 B2

Page 2

(51) Int. Cl.
*C09K 11/06* (2006.01)
*E21B 49/00* (2006.01)
*G01B 11/22* (2006.01)
*G01V 8/00* (2006.01)
*G01N 21/64* (2006.01)
*E21B 21/08* (2006.01)
*G01N 33/28* (2006.01)

(52) U.S. Cl.
CPC ............ *E21B 49/005* (2013.01); *G01B 11/22* (2013.01); *G01N 21/64* (2013.01); *G01N 33/2882* (2013.01); *G01V 8/00* (2013.01); C09K 2208/10 (2013.01); C09K 2211/1007 (2013.01); C09K 2211/1018 (2013.01); G01N 2021/6441 (2013.01)

(58) Field of Classification Search
CPC ............. C09K 2211/1018; E21B 21/08; E21B 49/005; G01B 11/22; G01N 21/64; G01N 33/2882; G01N 2021/6441; G01V 8/00
See application file for complete search history.

(56) References Cited

U.S. PATENT DOCUMENTS

| | | | |
|---|---|---|---|
| 8,680,866 B2 | 3/2014 | Marsala et al. | |
| 8,812,237 B2 | 8/2014 | Wilt et al. | |
| 9,260,957 B2 | 2/2016 | Commarieu et al. | |
| 9,366,099 B2 | 6/2016 | Ly | |
| 9,405,033 B2 | 8/2016 | Marsala et al. | |
| 9,611,736 B2 | 4/2017 | Marsala et al. | |
| 9,651,700 B2 | 5/2017 | Marsala et al. | |
| 9,696,450 B2 | 7/2017 | Marsala et al. | |
| 9,983,328 B2 | 5/2018 | Marsala et al. | |
| 10,125,586 B2 | 11/2018 | Balan et al. | |
| 10,132,952 B2 | 11/2018 | Marsala et al. | |
| 10,145,975 B2 | 12/2018 | Marsala et al. | |
| 10,156,654 B2 | 12/2018 | Marsala et al. | |
| 10,267,943 B2 | 4/2019 | Marsala et al. | |
| 10,377,938 B2 | 8/2019 | Sarkar et al. | |
| 10,408,045 B2 | 9/2019 | Cox | |
| 10,488,387 B2 * | 11/2019 | Waid | G01N 33/2835 |
| 10,570,716 B2 | 2/2020 | Balan et al. | |
| 10,612,360 B2 | 4/2020 | Al-Qasim et al. | |
| 10,677,034 B2 | 6/2020 | Balan et al. | |
| 10,677,035 B2 | 6/2020 | Balan et al. | |
| 10,808,529 B2 | 10/2020 | Ow et al. | |
| 2004/0108110 A1 | 6/2004 | Zupanick et al. | |
| 2005/0252286 A1 | 11/2005 | Ibrahim et al. | |
| 2009/0087911 A1 | 4/2009 | Rogerio | |
| 2010/0132448 A1 | 6/2010 | Donadille et al. | |
| 2010/0198519 A1 | 8/2010 | Wilt et al. | |
| 2012/0062886 A1 | 3/2012 | Piotti et al. | |
| 2012/0178653 A1 | 7/2012 | McClung, III | |
| 2012/0268135 A1 | 10/2012 | Marsala et al. | |
| 2012/0325465 A1 | 12/2012 | Hammer et al. | |
| 2014/0203810 A1 | 7/2014 | Marsala et al. | |
| 2014/0203811 A1 | 7/2014 | Marsala et al. | |
| 2014/0319379 A1 * | 10/2014 | Manian | G01N 21/6428 250/459.1 |
| 2014/0361777 A1 | 12/2014 | Marsala et al. | |
| 2015/0061683 A1 | 3/2015 | Marsala et al. | |
| 2015/0061684 A1 | 3/2015 | Marsala et al. | |
| 2015/0132543 A1 | 5/2015 | Nouzille et al. | |
| 2015/0232748 A1 | 8/2015 | Kanj et al. | |
| 2016/0291194 A1 | 10/2016 | Marsala et al. | |
| 2017/0059668 A1 | 3/2017 | Chang et al. | |
| 2017/0351000 A1 | 12/2017 | Marsala et al. | |
| 2018/0066515 A1 | 3/2018 | Marsala et al. | |
| 2018/0171782 A1 * | 6/2018 | Cox | E21B 47/11 |
| 2018/0275306 A1 | 9/2018 | Marsala et al. | |
| 2018/0298752 A1 | 10/2018 | Balan et al. | |
| 2018/0347349 A1 | 12/2018 | Marsala | |
| 2019/0003291 A1 | 1/2019 | Balan et al. | |
| 2019/0003292 A1 | 1/2019 | Balan et al. | |
| 2019/0011593 A1 | 1/2019 | Marsala et al. | |
| 2019/0169975 A1 | 6/2019 | Al-Qasim et al. | |
| 2019/0368336 A1 | 12/2019 | Hammond et al. | |
| 2019/0391034 A1 | 12/2019 | Al Jabri | |
| 2020/0030777 A1 | 1/2020 | Al-Jabri et al. | |
| 2020/0031738 A1 | 1/2020 | Al-Jabri et al. | |
| 2020/0032148 A1 | 1/2020 | Al-Jabri et al. | |
| 2020/0116019 A1 | 4/2020 | Ow et al. | |
| 2020/0208513 A1 | 7/2020 | Al-Qasim et al. | |

FOREIGN PATENT DOCUMENTS

| | | |
|---|---|---|
| WO | WO 2012115717 | 8/2012 |
| WO | WO 2014051789 | 4/2014 |
| WO | WO 2014060562 | 4/2014 |
| WO | WO 2014207075 | 12/2014 |
| WO | WO 2017136641 | 8/2017 |
| WO | WO 2018085504 | 5/2018 |
| WO | WO 2018234431 | 12/2018 |

OTHER PUBLICATIONS

Behnke et al., "Encapsulation of Hydrophobic Dyes in Polystyrene Micro- and Nanoparticles via Swelling Procedures," J. Fluoresc., 2011, 21(3):937-944.

Deschamps et al., "Drilling to the Extreme: the Micro-Coring Bit Concept," IADC/SPE 115187, presented at the IADC/SPE Asai Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . ," SPE 116554, Society of Petroleum Engineers, 2008 SPE Annual Technical Conference and Exhibition, Sep. 21-24, 2008, 19 pages.

Georgi, et al., "Advances in Cuttings Collection and Analysis," SPWLA 34th Annual Logging Symposium, Jun. 13-16, 1993, 20 pages.

Musyanovych et al., "Preparation of Biodegradable Polymer Nanoparticles by Miniemulsion Technique and Their Cell Interactions," Macromolecular Bioscience, Feb. 2008, 8(2):127-139.

Reisch et al., "Fluorescent Polymer Nanoparticles Based on Dyes: Seeking Brighter Tools for Bioimaging," Small, Apr. 2016, 12(15):1968-1992, 48 pages.

Santarelli et al., "Formation Evaluation From Logging on Cuttings," SPE Reservoir Evaluation and Engineering, presented at the 1996 SPE Permian Basin Oil and Gas Recovery Conference, Mar. 27-29, 1996, 7 pages.

Vollrath et al., "Fluorescence imaging of cancer tissue based on metal-free polymeric nanoparticles—a review," J. Mater. Chem. B, Mar. 2013, 1(15):1994-2007.

PCT International Search Report and Written Opinion in International Appln. No. PCT/US2021/046916, dated Nov. 17, 2021, 14 pages.

Poitzsch et al., "Nanoparticle Tags for Improved Depth Correlation," IPTC-19785, International Petroleum Technology Conference (IPTC), IPTC Conference 2020, 2 pages (abstract only).

* cited by examiner ically different from the emission wavelength of each other fluorescent dye, an excitation wavelength different from the excitation wavelength of each other fluorescent dye, or both.
FLUORESCENT DYE LOADED POLYMERIC TAGGANTS FOR DEPTH DETERMINATION IN DRILLING WELLS

BACKGROUND

Surface logging (as known as mud logging) is the creation of a detailed record (well log) of a borehole by examining the cuttings of rock brought to the surface by the circulating drilling fluid (most commonly drilling mud). Surface logging provides well owners and producers with information about the lithology and fluid content of the borehole while drilling. Under some circumstances, foam or compressed air is employed as a circulating drilling fluid, rather than mud.

SUMMARY

In an aspect, a method of surface logging a well includes adding each of multiple polymeric taggants to a circulating drilling fluid in an addition sequence while drilling the well. Each polymeric taggant includes a polymer and a respective fluorescent dye, and each fluorescent dye has an emission wavelength different from the emission wavelength of each other fluorescent dye, an excitation wavelength different from the excitation wavelength of each other fluorescent dye, or both. The method includes taking a sample of drill cuttings carried by a drilling fluid while drilling a well in the presence of the drilling fluid, wherein the sample of drill cuttings includes polymeric taggants attached to the drill cuttings. The method includes extracting the dyes from the sample of drill cuttings into an extract solution; determining an indication of the type of and the concentration of each of the dyes in the extract solution; and determining a depth associated with the sample of drill cuttings based on the indication of the concentration of each of the dyes and on the addition sequence.

Embodiments can include one or any combination of two or more of the following features.

Each polymeric taggant includes polymeric nanoparticles.

The method includes determining an indication of the type and the concentration of each of the fluorescent dyes in the extract solution based on an excitation spectrum of the extract solution, an emission spectrum of the extract solution, or both.

Determining an indication of the type and the concentration of each of the fluorescent dyes includes analyzing the extract solution with a fluorimeter or an ultraviolet spectrometer.

Determining an indication of the type and the concentration of each of the fluorescent dyes includes: illuminating the extract solution; and collecting an emission spectrum from the extract solution responsive to the illumination. The method includes determining an intensity of the emission spectrum at the emission wavelength of each of the fluorescent dyes; and determining the indication of the concentration of each of the fluorescent dyes based on the respective intensities.

The method includes determining an indication of the type and the concentration of each of the fluorescent dyes in the extract solution using mass spectrometry.

The method includes determining an indication of the concentration of the polymer of the polymeric taggant in the extract solution using mass spectrometry.

Extracting the fluorescent dyes includes dissolving the polymer of the polymeric taggant in a solvent.

The polymer of one or more of the polymeric taggants includes a styrene based polymer.

The polymer of one or more of the polymeric taggants includes a polysaccharide based polymer.

The polymer of one or more of the polymeric taggants includes a polymer based on an acrylate, a polyester, a polyamide, or a polycarbonate.

One or more of the polymeric taggants includes polymeric nanoparticles with the respective fluorescent dye attached to a polymer of the nanoparticles.

One or more of the polymeric taggants includes polymeric nanoparticles with the respective fluorescent dye encapsulated in an interior of the nanoparticles.

One or more of the polymeric taggants includes a polymer with the respective fluorescent dye attached to the polymer.

At least some of the polymeric taggants attach to the drill cuttings during generation of the drill cuttings.

The method includes using pyrolysis-gas chromatography-mass spectrometry to analyze properties of the drill cuttings.

The method includes performing nuclear-based porosity or mineralogy analysis on the drill cuttings.

In an aspect, a composition includes drill cuttings obtained from a drilling well; and one or more polymeric taggants attached to the drill cuttings. Each polymeric taggant includes a polymer and a respective fluorescent dye, and each fluorescent dye has an emission wavelength different from the emission wavelength of each other fluorescent dye, an excitation wavelength different from the excitation wavelength of each other fluorescent dye, or both.

Embodiments can include one or any combination of two or more of the following features.

The polymer of one or more of the polymeric taggants includes a styrene based polymer.

The polymer of one or more of the polymeric taggants includes a polysaccharide based polymer.

The polymer of one or more of the polymeric taggants includes a polymer based on an acrylate, a polyester, a polyamide, or a polycarbonate.

One or more of the polymeric taggants includes polymeric nanoparticles with the respective fluorescent dye attached to a polymer of the nanoparticles.

One or more of the polymeric taggants includes polymeric nanoparticles with the respective fluorescent dye encapsulated in an interior of the nanoparticles.

One or more of the polymeric taggants includes a polymer with the respective fluorescent dye attached to the polymer.

At least some of the polymeric taggants are adhered to a surface of the drill cuttings.

At least some of the polymeric taggants are penetrated within the drill cuttings.

The polymeric nanoparticles and fluorescent dyes are soluble in a common organic solvent.

The details of one or more implementations are set forth in the accompanying drawings and the description below. Other features and advantages will be apparent from the description and drawings, and from the claims.

DETAILED DESCRIPTION

We describe here approaches to surface logging used for analysis of formations while drilling wells. In these approaches, multiple types of fluorescent dye loaded polymeric taggants, such as polymeric nanoparticle taggants, are injected into circulating drilling fluid according to a sequence. The fluorescent dye loaded polymeric taggants attach to drill cuttings as the drill cuttings are produced by operation of a downhole drill bit. When the drill cuttings return to the surface, the drill cuttings are analyzed to identify which types of fluorescent dye loaded polymeric taggants are attached to the drill cuttings. For instance, excitation spectra, emission spectra, or both can be used to identify the types of fluorescent dye loaded polymeric taggants that are present in a given sample of drill cuttings. Based on the sequence of injection of the fluorescent dye loaded polymeric taggants and the relative concentrations of each type of taggant attached to a given sample of drill cuttings, the depth of origin of the drill cuttings can be determined. In this description, we sometimes use the phrase polymeric taggants to encompass polymeric taggants such as polymeric nanoparticle taggants.

The attachment of the fluorescent dye loaded polymeric taggants, such as polymeric nanoparticle taggants, to the drill cuttings enables depth information to be determined accurately both in real time, for instance on site at the drilling well, and later, even if the drill cuttings are shifted or scrambled during transport or storage, or if settling of the drill cuttings occurs. In addition, by loading polymeric taggants with fluorescent dyes, the dyes, incorporated into or onto the polymer (such as the polymer of the nanoparticles), can be separated easily from the dirty drilling mud, facilitating analysis of the dyes and leading to more accurate results. For instance, the polymeric taggants that are loaded with the fluorescent dyes can be extracted from the drilling fluid using organic solvents.

Figure 1:
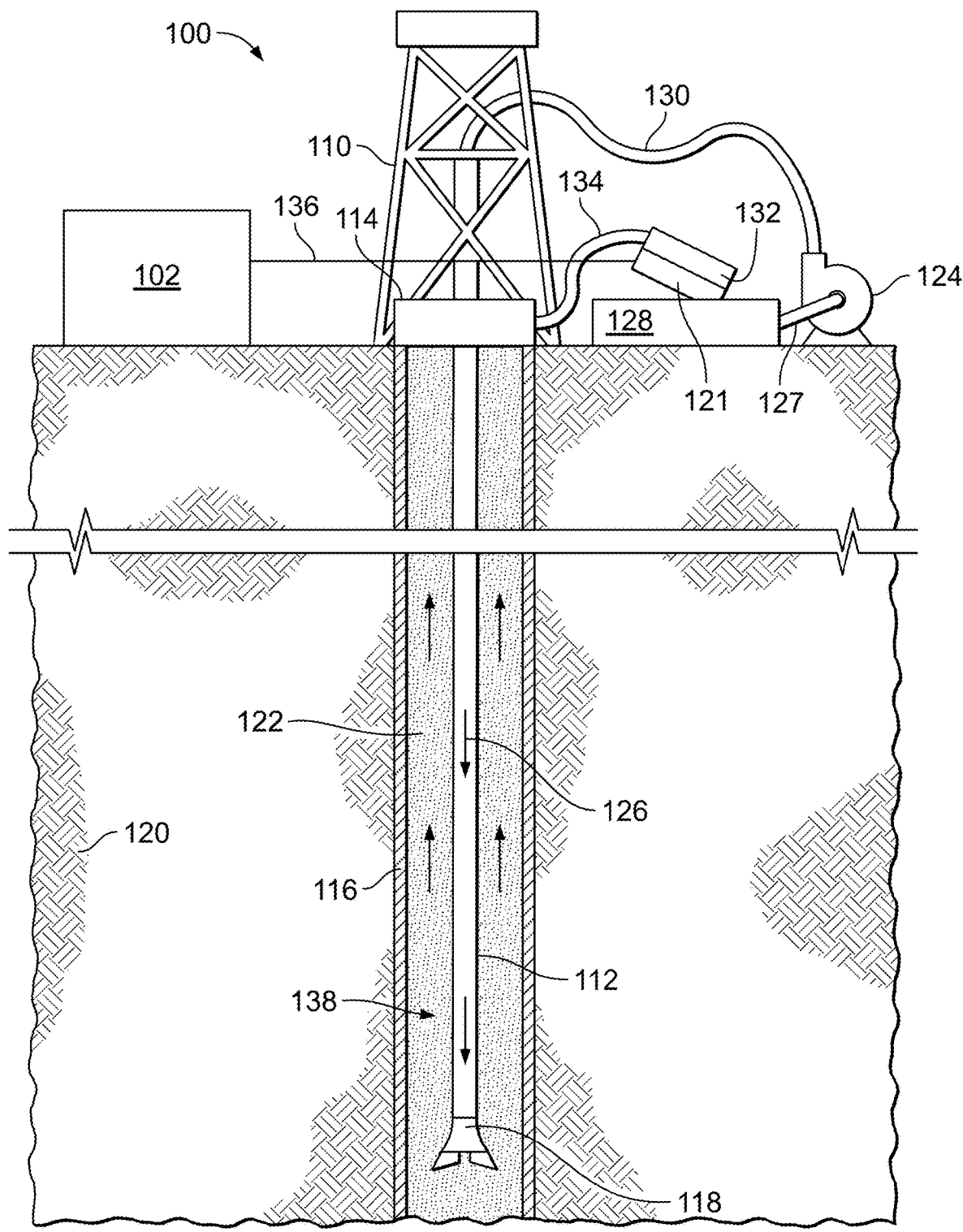
FIG. 1 is a diagram of a surface logging operation.

FIG. 1 shows a drilling system 100 and an associated surface logging unit 102. The drilling system 100 includes a derrick 110 that supports the weight of and permits selective positioning of a drill string 112 through a blowout preventer 114 at the wellhead of a wellbore 116. The drill string 112 has a downhole end coupled to a drill bit 118 operable to drill the wellbore 116 in a formation 120. To facilitate drilling and removal of drill cuttings 122, a circulation pump 124 circulates drilling fluid 126 though the wellbore 116. An inlet of a circulation pump 124 is coupled to a reservoir for the drilling fluid through a first pipe 127. In the illustrated system, the reservoir is a mud pit 128. In some systems, reservoir can be, for example, a tank or tanks. A pump discharge of the circulation pump 124 is coupled to a top end of the drill string 112 through a second pipe 130. The blowout preventer 114 is coupled to a shaker table 132 through a third pipe 134. The mud pit 128 is coupled to the shaker table 132 and receives the drilling fluid 126 from the shaker table 132.

In the case of real-time well-site logging of cuttings, a suction line 136 or other continuous transfer line couples the surface logging unit 102 with the shaker table 132. The surface logging unit 102 includes analytical equipment operable to identify fluorescent dye loaded polymeric taggants 138, such as polymeric nanoparticle taggants, associated with the drill cuttings 122 and perform petro-physical analysis on the drill cuttings 122. For example, the surface logging unit 102 includes a mass spectrometer (e.g., a pyrolysis-GCMS), a densitometer, an X-ray diffractometer, a fluorescence spectrometer, an ultraviolet (UV) spectrometer, other mineralogical analysis instruments, as well as sample cleaning equipment. Identification of the fluorescent dye loaded polymeric taggants is used to determine the depth from which the drill cuttings originated.

The surface logging unit 102 is onsite and directly coupled to the drilling fluid circulation system. This configuration facilitates near-real-time depth information. For example, an onsite surface logging unit directly coupled to the drilling fluid circulation can provide depth correlation for drill cuttings within minutes after delivery of samples of the drill cuttings. In some examples, analysis of samples is performed remotely from the drilling site.

During drilling, the drilling fluid 126 is pumped from the mud pit 128 and flows through the first pipe 127 into the pump suction of the circulation pump 124. The circulation pump 124 then pumps the drilling fluid 126 from the pump discharge to the top end of the drill string 112 through the second pipe 130. The sequence of fluorescent dye loaded polymeric taggants 138 is introduced into the drilling fluid 126 between the circulation pump 124 and the blowout preventer 114 or between the mud pit 128 and the circulation pump 124.

The drilling fluid 126 carrying the fluorescent dye loaded polymeric taggants 138 flows downhole in the drill string 112 through the wellhead and the blowout preventer 114 and enters the wellbore 116 through the drill bit 118. As the drilling fluid 126 exits the drill bit 118, the fluorescent dye loaded polymeric taggants 138 attach to the drill cuttings 122 being produced by the drill bit 118. The drilling fluid 126 flows through the wellbore annulus toward the wellhead while carrying the drill cuttings 122 and the attached fluorescent dye loaded polymeric taggants 138. The drilling fluid 126 flows through the blowout preventer 114 to the shaker table 132 through the third pipe 134. The shaker table 132 removes the drill cuttings 122 and the attached fluorescent dye loaded polymeric taggants 138 from the drilling fluid 126 before the drilling fluid 126 flows to the mud pit 128. At least a portion of the drill cuttings 122 and the attached fluorescent dye loaded polymeric taggants 138 are transferred to the surface logging unit 102 for analysis to identify the depth of origin and petro-physical properties of the drill cuttings 122.

While the illustrated implementation shows a vertical wellbore, the principles of this disclosure can also be applied to a deviated or horizontal wellbore or to a drilling system that uses coiled tubing drilling.

Figure 2:
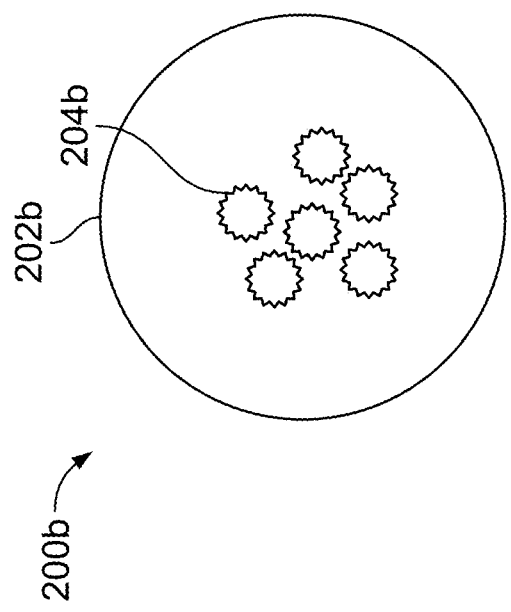
FIG. 2 is a diagram of fluorescent dye loaded nanoparticle taggants.
Figure 2:
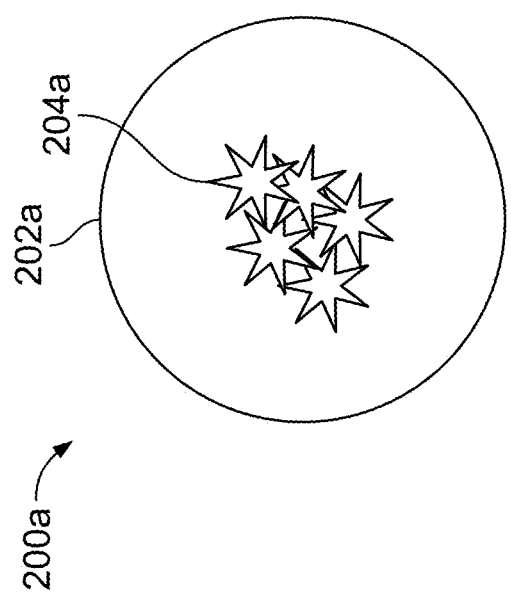

Referring to FIG. 2, in an example, the fluorescent dye loaded polymeric taggants include multiple types of fluorescent dye loaded polymeric nanoparticle taggants 200a, 200b. Each type of polymeric nanoparticle taggant 200a, 200b includes polymeric nanoparticles 202a, 202b (collectively referred to as nanoparticles 202) that contain fluorescent dye 204a, 204b. Each fluorescent dye 204a, 204b (collectively referred to as fluorescent dyes 204) has an excitation spectrum (for instance, a peak excitation wavelength) that differs from the excitation spectrum of each other fluorescent dye 204, an emission spectrum (for instance, a peak emission wavelength) that differs from the emission spectrum of each other fluorescent dye 204. In the example of FIG. 2, the fluorescent dyes 204 are encapsulated in the interior of the respective nanoparticles 202. In some examples, the fluorescent dyes 204 are attached to the polymer of the respective nanoparticles 202. The nanoparticles 202 are formed of a polymer, such as a styrene-based polymer, acrylate-based polymer, polyester, polyamide, polycarbonate, or other type of polymers. The composition of the nanoparticles 202 and the fluorescent dyes 204 is discussed further infra.

Figure 3:
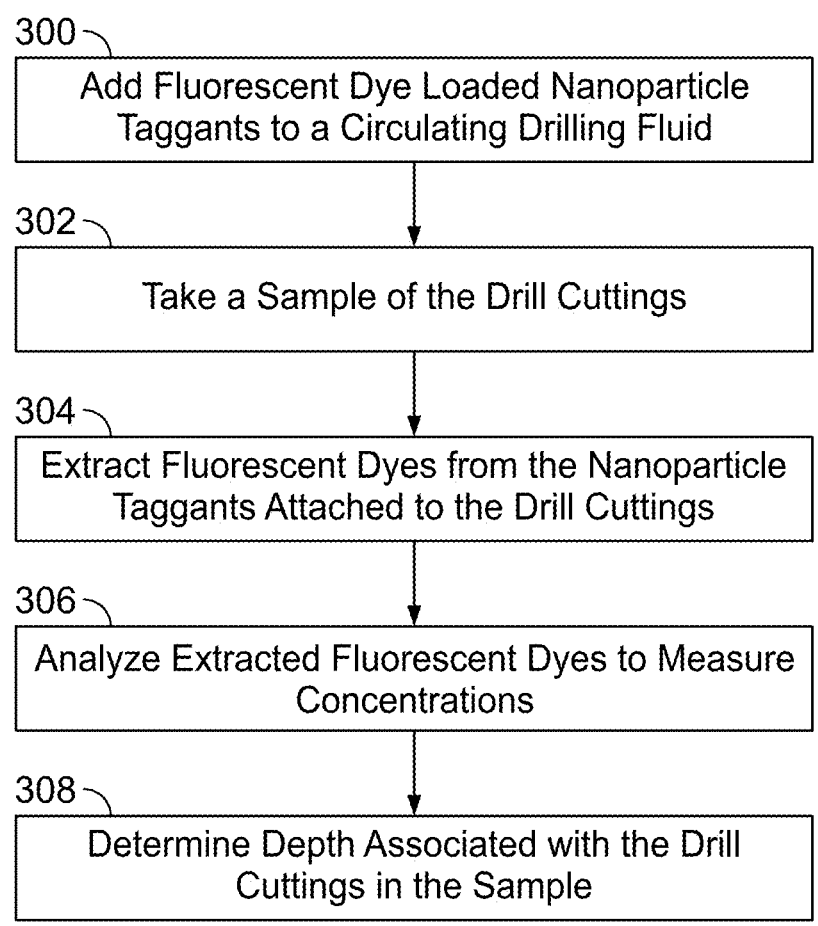
FIG. 3 is a flow chart.

FIG. 3 illustrates an example method for identifying the depth of origin and petro-physical properties of drill cuttings using fluorescent dye loaded polymeric taggants. The method is described with respect to the drilling system 100 and surface logging unit 102 of FIG. 1. Generally, multiple types of fluorescent dye loaded polymeric taggants, such as polymeric nanoparticle taggants, are injected into the circulated drilling fluid in a predefined sequence. The fluorescent dye loaded polymeric taggants attach to drill cuttings, and the drill cuttings then are analyzed to identify which type or types of fluorescent dye loaded polymeric taggants are attached thereto. Based on the injection sequence and the identified type or types of fluorescent dye loaded polymeric taggants, the depth of origin of the drill cuttings can be determined.

The surface logging unit 102 performs surface logging as a drilling system 100 is used to form a wellbore 116. Multiple types of fluorescent dye loaded polymeric taggants 138 are added to circulating drilling fluid 126 in a sequence while drilling proceeds (300). For instance, each type of fluorescent dye loaded nanoparticle taggant includes polymeric nanoparticles having respective type of fluorescent dye encapsulated within or attached to the polymers of the nanoparticles. The fluorescent dye of each type of polymeric taggant has an excitation spectrum that differs from the excitation spectrum of the fluorescent dye of each other type of polymeric taggant, an emission spectrum that differs from the emission spectrum of the fluorescent dye of each other type of polymeric taggant, or both. The fluorescent dye loaded polymeric taggants 138 are added to the drilling fluid 126 between the circulation pump 124 and the blowout preventer 114. The sequence of types of fluorescent dye loaded polymeric taggants added to the drilling fluid 126 can be a repeating sequence in which the sequence restarts after the last taggant type in the sequence is added to the drilling fluid.

The addition can include injecting a first type of fluorescent dye loaded polymeric taggant for a first period of time, such as for between 30 and 180 seconds, before switching to a second type of fluorescent dye loaded polymeric taggant. In some examples, the switching includes waiting for a period of time, such as for between 60 and 240 seconds, after stopping injection of the first type of fluorescent dye loaded polymeric taggant before starting injection of the next type of fluorescent dye loaded polymeric taggant. Further description of the injection of taggants is provided in US 2020/0116019, the entire contents of which are incorporated here by reference.

Some of the fluorescent dye loaded polymeric taggants attach to the drill cuttings 122 during generation of drill cuttings, such as by adhering to the drill cuttings, penetrating into the drill cuttings, or both. When the circulating drilling fluid 126 returns to the surface, samples of the drill cuttings 122 are taken (302). For instance, the samples are taken after the drilling fluid returns to the surface and before the drilling fluid returns to a mud pit or other reservoir. In some examples, taking the samples includes bagging cuttings at intervals of between 5 and 8 meters in advance of the wellbore. In some examples, taking the samples includes taking samples of the circulating drilling fluid 126 that includes drill cuttings.

Each sample includes drill cuttings with attached fluorescent dye loaded polymeric taggants. The fluorescent dyes in the taggants are extracted by exposing the sample to a solvent in which the polymer of the taggants (for instance, the polymeric nanoparticles) and the fluorescent dyes are both soluble (304). Exposure to the solvent dissolves the polymer (for instance, the polymeric nanoparticles) and the dyes.

Each sample, now including dissolved fluorescent dyes, is analyzed to determine the type of each of the dyes in the sample and to measure concentrations of each of the types of dyes (306). Analysis can be performed by fluorimetry, gas chromatography mass spectrometry (GC-MS), ultraviolet (UV) spectrometry, digital photography to record transit of the nanoparticles upon excitation with ultraviolet light, or another analysis method. For instance, for fluorimetry or UV spectrometry analysis, an emission or excitation spectrum of the sample is determined, and the types of fluorescent dyes present in the sample are identified based on the wavelengths of peaks in the emission or excitation spectrum. The concentration of each dye can then be determined, either absolutely or relative to the concentration of each other dye, based on the intensity of the peaks in the spectrum. A given taggant is positively identified as present when the concentration of that fluorescent dye from that taggant is significantly (for instance, more than three times) greater than any background "noise" signals from natural geological species or cross-pollution from taggants in reused drilling mud.

Based at least in part on the measured concentrations of each type of fluorescent dye and on the injection sequence, depths associated with the drill cuttings in the samples are identified (308), as discussed in further detail infra. For instance, the downward trip time and upward return trip time for the circulating drilling fluid and for each type of fluorescent dye loaded polymeric taggants can be calculated, enabling individual types of fluorescent dye loaded polymeric taggants in the sequence to be correlated with specific depths. Because the fluorescent dye loaded polymeric taggants are attached to the drill cuttings, the depth of origin of the drill cuttings can be determined even if the drill cuttings are shifted or scrambled in transport or storage, allowing depth determination with a high degree of accuracy.

The method illustrated in FIG. 3 can be used when the drilling system 100 uses drilling mud as a drilling fluid. The method can also be used when the drilling system 100 uses foam as a drilling fluid. Using fluorescent dye loaded polymers, such as polymeric nanoparticles, as taggants can enable surface logging of drilling using light underbalanced foams since some polymers are similar in density to water. For example, polystyrene has a density of approximately 1.04 grams per cubic centimeter (g/cc) and polymethacrylate has a density of approximately 1.18 g/cc. In contrast, denser taggants such as silica or metal oxides with density equal to or more than 2× that of water are not usable with light underbalanced foams.

Figure 5:
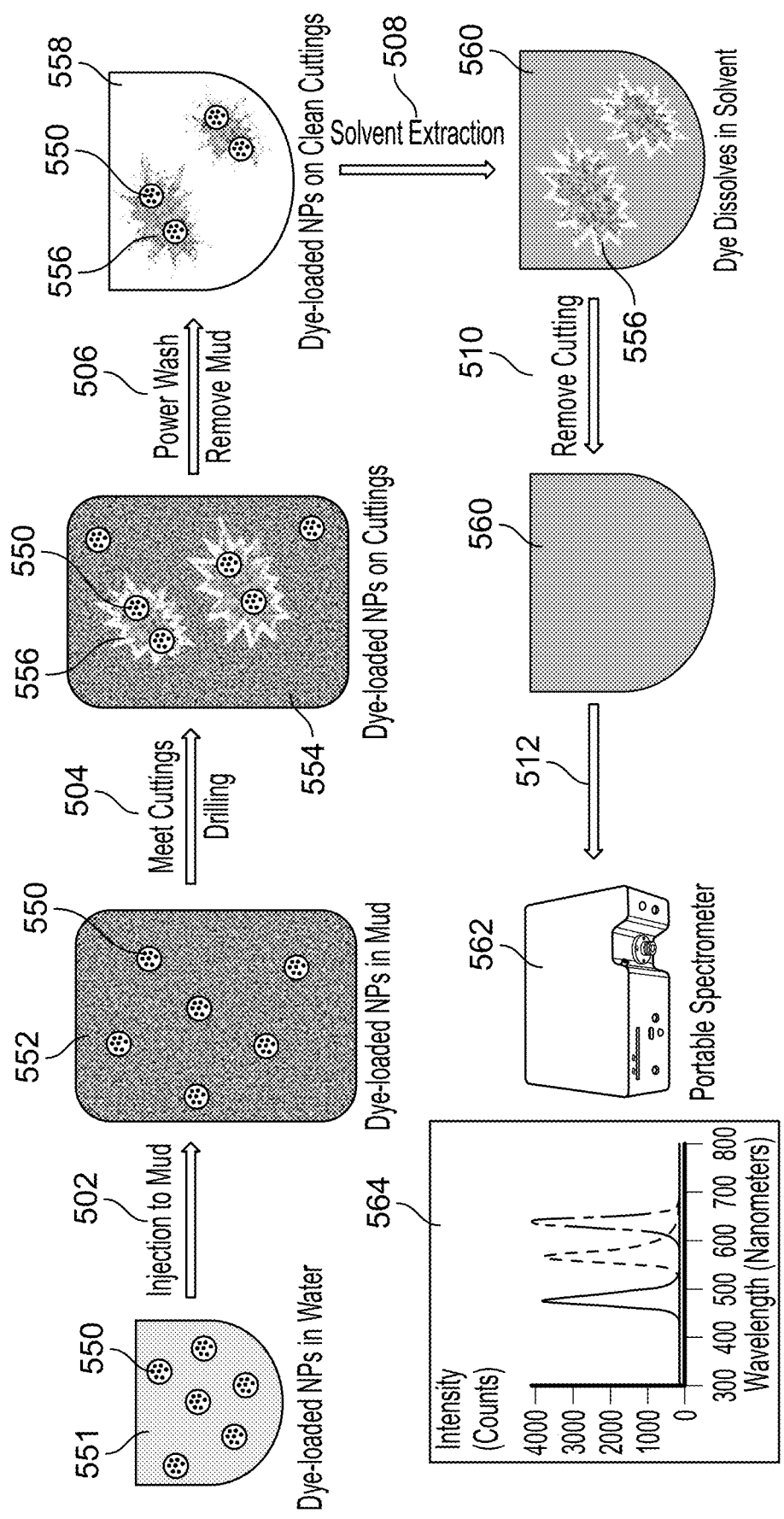
FIG. 5 is a diagram of a process for depth determination.

FIG. 5 shows an example workflow for using fluorescent dye loaded polymeric nanoparticle taggants for depth determination. A similar workflow can be followed for non-nanoparticle polymeric taggants. Multiple types of fluorescent dye loaded nanoparticle taggants 550 loaded with respective types of fluorescent dyes are each dispersed in water, forming multiple colloidal suspensions 551. Each type of fluorescent dye has an emission spectrum that differs from the emission spectrum of each other type of fluorescent dye, an excitation spectrum that differs from the excitation spectrum of each other type of fluorescent dye, or both. Examples of fluorescent dyes that can be used in conjunction with polymeric nanoparticles as taggants are given in Table 1:

TABLE 1

Fluorescent dyes for use in conjunction with polymeric nanoparticles as taggants for depth measurements.

| Dye | Excitation Color | Max. excitation wavelength (nm) |
|---|---|---|
| Fluorescein isothiocyanate (FITC) | green | 518 |
| Solvatochromic Nile red | red (red to gold) depending on the solvent polarity | 552 |
| Dipicolinic acid | purple | 360 |
| Fluorescein | green | 495 |
| Pyrene | blue | 373, 385 |
| Rhodamine | red | 705 |
| Cyanine-5 | far-red | 660 |
| Pyrromethene 567 | | 522 |
| 9,10-diphenylanthracene | blue | 350 |

The colloidal suspensions are injected sequentially (for instance, in the sequence depicted in FIG. 4, discussed infra) into circulating drilling fluid, such as water-based drilling mud (502). For instance, the colloidal dispersion of each type of fluorescent dye loaded nanoparticle taggant is formed at a concentration of between 500 and 1500 ppm and is injected into the drilling fluid at a rate of between 1 and 10 liters per minute. After injection of the fluorescent dye loaded nanoparticle taggants, drilling fluid 552, such as drilling mud, includes the fluorescent dye loaded nanoparticle taggants 550. In some examples, a manifold of tanks is provided, each containing a colloidal dispersion of a respective type of fluorescent dye loaded nanoparticle taggant. The tanks are switched in an automated, regular cycle into an injection pump, enabling rapid switching between taggants according to the predetermined sequence.

Figure 4:
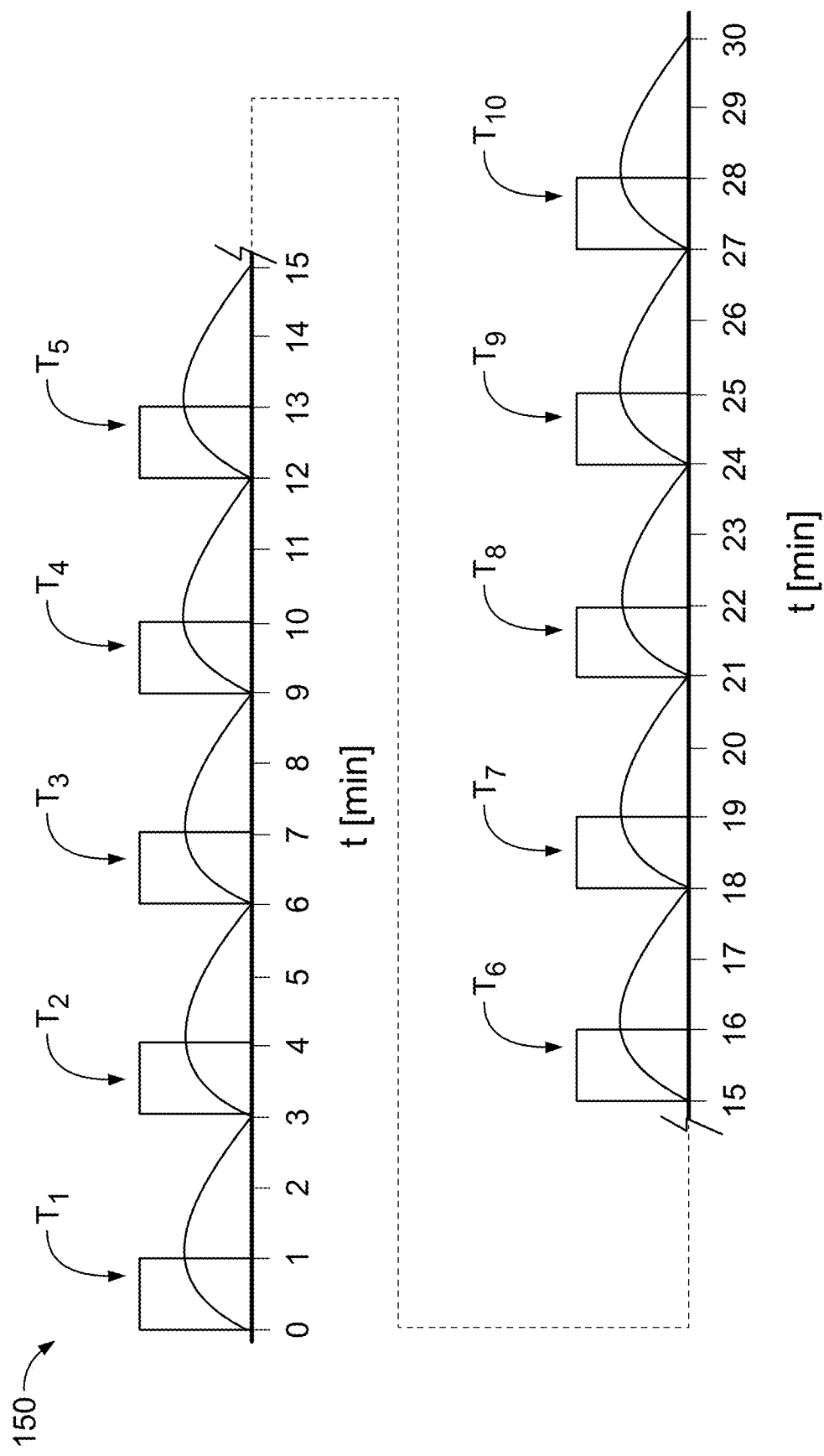
FIG. 4 is a diagram of a taggant injection sequence.

FIG. 4 shows a specific example of a sequence 150 of ten distinct fluorescent dye loaded polymeric taggants being introduced into drilling fluid. In the sequence 150, the taggants (T1 . . . T10) are introduced in pulses with each taggant being added for one minute followed by a two-minute pause before addition of the next taggant begins. Other sequences may have other numbers of taggants or different delivery timings. The number of the taggants in the sequence, the timing of their delivery, and the delivery concentrations are determined based on factors including, for example, the drilling rate, the feasible taggant injection rate into the mud pipe, the fluid circulation rate, the drill string/tubing inner diameter (ID) and the taggant detection sensitivity limits.

Referring again to FIG. 5, a sample of drill cuttings 554 is obtained (504), for instance, from circulating drilling fluid or from drilling fluid returned to the surface. The sample 554 includes the fluorescent dye loaded nanoparticle taggants 550 attached to drill cuttings 556 and dispersed in the drilling fluid, such as drilling mud. In some examples, fewer than all the fluorescent dye loaded nanoparticle taggants are attached to drill cuttings 556.

The sample of drill cuttings is cleaned (506), for instance, by power washing, to remove the mud, leaving a cleaned sample 558 including the fluorescent dye loaded nanoparticle taggants 550 on clean drill cuttings 556. A solvent is added to the cleaned sample (508) and the polymeric nanoparticles are dissolved in the solvent, releasing the fluorescent dyes into solution. The result is a solution 560 of fluorescent dye, with the drill cuttings 556 suspended in the solution 560. The solvent is a solvent in which both the fluorescent dye and the polymer of the nanoparticles are soluble. For instance, the solvent can be an organic solvent, such as tetrahydrofuran, chloroform, dichloromethane, toluene, xylene, benzene, dimethylformamide, or another solvent.

The drill cuttings are removed from solution (510), for instance, by filtering or centrifuging, leaving the solution 560 of fluorescent dye without drill cuttings. For instance, centrifugation pushes the cuttings and fine particles to the bottom of a centrifugation vial. The solution 560 then can be pipetted off the top of the vial and transferred elsewhere, leaving behind the cuttings.

The solution 560 is analyzed (512) to determine the type of each fluorescent dye in the solution 560 and to measure the concentration of each of the individual types of fluorescent dyes. The measured concentrations are used, along with the sequence with which the nanoparticles were injected, to determine the depth associated with the sample 554. In the example of FIG. 5, the analysis is performed by a portable UV spectrometer 562 that produces an emission spectrum 564 as an output. The intensity of each emission peak is indicative of the concentration of the fluorescent dye having an emission wavelength corresponding to the wavelength of the emission peak. The portable spectrometer 562 can be located at the site of the drilling well, such as on the drilling rig, providing substantially real time information about drilling depths. Other types of analysis that can be performed in addition to or instead of UV spectrometry include fluorimetry, GC-MS, digital photography, or other analysis techniques. The analysis can be performed on-site at the drilling well or at an off-site laboratory.

Figure 6:
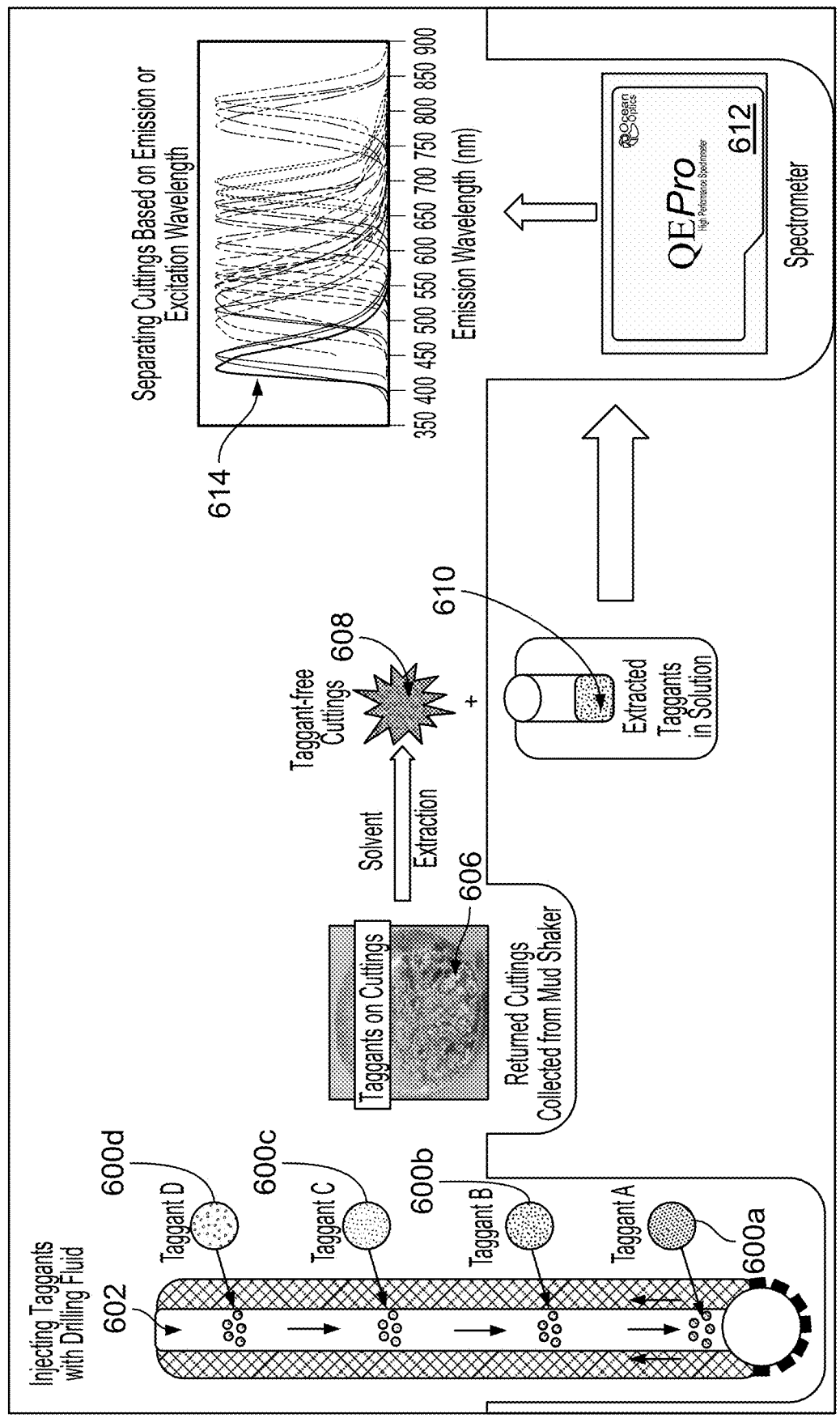
FIG. 6 is a diagram of a process for depth determination.

Referring to FIG. 6, in a specific example, multiple types 600a-600d of fluorescent dye loaded nanoparticle taggants are injected into a drilling well 602. The first type 600a was injected first in the injection sequence, followed by the second type 600b, the third type 600c, and finally the fourth type 600d. Thus, the first type 600a of fluorescent dye loaded nanoparticle taggant has the shallowest penetration, and the fourth type 600d penetrates deepest into the drilling well.

Drill cuttings that return to the surface are tagged with the fluorescent dye loaded nanoparticle taggants, for instance, with the fluorescent dye loaded nanoparticle taggants attached to the surface of the drill cuttings or penetrated into the drill cuttings. The drill cuttings are cleaned, and cleaned cuttings 606 are collected, for instance, from a mud shaker. Following solvent extraction, the fluorescent dye loaded nanoparticle taggants are removed from the drill cuttings, leaving untagged drill cuttings 608 and a solution 610 extracted fluorescent dyes.

The solution 610 is analyzed using one or more analysis techniques. In the example of FIG. 6, the analysis is a UV spectrometry analysis using a UV spectrometer 612 that outputs an emission or excitation spectrum 614 of the solution 610. Each peak or set of peaks in the spectrum corresponds to one of the fluorescent dyes. The relative intensities of the peaks in the spectrum is indicative of the concentration of each of the dyes in the solution 610, which in turn can be used, in combination with the injection sequence, to determine the depth in the drilling well 602 from which the drill cuttings 604 originated.

In some examples, fluorimetry or UV spectrometry is used for identification of the fluorescent dyes, and other analysis techniques, such as pyrolysis-GCMS, are used to analyze properties of the drill cuttings. This enables the origin depth of drill cuttings to be correlated with properties of drill cuttings from that depth. In some examples, nuclear-based porosity or mineralogy analyses are performed on the drill cuttings. In contrast to elemental taggants, taggants composed of fluorescent dye loaded polymeric nanoparticles typically do not interfere with analyses such as, for example, x-ray refraction or other nuclear-based porosity or mineralogy analyses conventionally performed on reservoir rock cores and drill cuttings.

The fluorescent dye loaded nanoparticle taggants can be formed by emulsion polymerization of monomers, such as styrenic monomers or acrylic monomers, with fluorescent dyes incorporated into the micelles of the emulsion, or can be polyesters, polyamides, polycarbonates, or other types of polymers. Further description of emulsion polymerization is provided in US 2020/0116019, the entire contents of which are incorporated here by reference. The fluorescent dye loaded nanoparticle taggants can be formed using a water miscible solution of a polymer containing the fluorescent dye. The fluorescent dye loaded nanoparticle taggants can be formed by swelling dyes, such as hydrophobic dyes, into polymer nanoparticles. The fluorescent dye loaded nanoparticles can be formed by emulsification-solvent evaporation. In some examples, fluorescent dyes such as fluorescein isothiocyanate (FITC) can be covalently attached to amine modified styrenic or acrylate nanoparticles by reaction between isothiocyanate and amine.

Styrenic monomers can include, for instance, 4-Acetoxystyrene, 4-Benzhydrylstyrene, 4-Benzyloxy-3-methoxystyrene, 4-tert-Butoxystyrene, 4-Bromostyrene, 4-Chlorostyrene, 2,6-Dichlorostyrene, 2,6-Difluorostyrene, 3,4-Dimethoxystyrene, 2,4-Dimethylstyrene, 4-Ethoxystyrene, 4-Flourostyrene, 4-Methylstyrene, α-Methylstyrene, Pentafluorophenyl 4-vinylbenzoate, 2,3,4,5,6-Pentafluorostyrene, 4-(Trifluoromethyl)styrene, 2,4,6-Trimethylstyrene, 4-Methoxystyrene, 4-Vinylbenzocyclobutene, 4-Chloromethylstyrene, 4-Vinylbiphenyl, 4-Vinylbenzoic acid, 1,1-Diphenylethylene, 3,5-Bis(trifluoromethyl)styrene, 4-Vinylphenyl acetate, and Trimethoxy(4-vinylphenyl)silane. Aminostyrenic monomers include, but are not limited to, (1S)-1-(3-vinylphenyl)-1,2-ethanediamine and 4-vinylphenol.

Acrylic monomers can be methacrylic monomers, such as 1-naphthyl methacrylate, pentabromophenyl methacrylate, phenyl methacrylate, propyl methacrylate, stearyl methacrylate, 3-sulfopropyl methacrylate potassium salt, tetrahydrofurfuryl methacrylate, 3,3,5-trimethylcyclohexyl methacrylate, 1,1,1,3,3,3-hexafluoroisopropyl methacrylate, 2,2,3,4,4,4-hexafluorobutyl methacrylate, 2,2,3,3,4,4,4-heptafluorobutyl methacrylate, 2-[(1',1', 1'-trifluoro-2'-(trifluoromethyl)-2'-hydroxy)propyl]-3-norbornyl methacrylate, 2,2,2-trifluoroethyl methacrylate, 3,3,4,4,5,5,6,6,7,7,8,8,8-tridecafluorooctyl methacrylate, 2,2,3,3-tetrafluoropropyl methacrylate, 2,2,3,3,3-Pentafluoropropyl methacrylate, 2,2,3,3,4,4,5,5-Octafluoropentyl methacrylate, and 1,1,1,3,3,3-Hexafluoroisopropyl methacrylate.

In some examples, the nanoparticle taggants are formed by reacting amine-containing styrenic monomers, such as 4-Vinylaniline, with epoxide monomers, such as 1,2-Epoxybutane, 1,2-Epoxypentane, 1,2-Epoxyhexane, 1,2-Epoxyoctane, 1,2-Epoxydodecane, 1,2-Epoxytetradecane, 1,2-Epoxyhexadecane, 2-Hexadecyloxirane, Allyl glycidyl ether, Butyl glycidyl ether, tert-Butyl glycidyl ether, 3,4-Epoxy-1-butene, 1,2-Epoxy-5-hexene, 1,2-Epoxy-9-decene, 4-Chlorophenyl glycidyl ether, 1,2-Epoxy-3-phenoxypropane, (2,3-Epoxypropyl)benzene, 2-Ethylhexyl glycidyl ether, Furfuryl glycidyl ether, Glycidyl hexadecyl ether, Glycidyl isopropyl ether, Glycidyl 4-methoxyphenyl ether, Glycidyl 2-methylphenyl ether, Glycidyl 2,2,3,3,4,4,5,5-octafluoropentyl ether, 2,3-Epoxy-1-(1-ethoxyethoxy)propane, 1,2-Epoxydecane, 1,2-Epoxyoctadecane, 1,2-Epoxyeicosane, 2,2,3,3,4,4,5,5,5-Nonafluoropentyloxirane, 2,2,3,3,4,4,5,5,6,6,7,7,7-Tridecafluoroheptyloxirane, 1,2-Epoxy-1H,1H,2H,3H,3H-heptadecafluoroundecane, Glycidyl methyl ether, Ethyl glycidyl ether, Epichlorohydrin, Glycidyl propargyl ether, Glycidyl lauryl ether, tert-Butyldimethylsilyl (S)-glycidyl ether, 3-Glycidyloxypropyltrimethoxysilane, 3-Glycidyloxypropyl(dimethoxy)methylsilane, [8-(Glycidyloxy)-n-octyl]trimethoxysilane, Triethoxy(3-glycidyloxypropyl)silane, Diethoxy(3-glycidyloxypropyl)methylsilane, 1,1,1,3,5,5,5-Heptamethyl-3-(3-glycidyloxypropyl)trisiloxane, 3-[2-(Perfluorohexyl)ethoxy]-1,2-epoxypropane, Benzyl glycidyl ether, 4-tert-Butylphenyl glycidyl ether, 2,4-Dibromophenyl glycidyl ether, (S)-Glycidyl titryl ether, (S)—N-Glycidylphthalimide, and 4-Glycidyloxycarbazole.

A library of fluorescent dye loaded nanoparticle taggants can be generated by various combinations of monomers (for nanoparticle formation, for instance by emulsion polymerization) and fluorescent dye. Examples of combinations of monomers and fluorescent dyes are given in Table 2. Other combinations can also be used, and monomers, dyes, or both other than those listed in Table 2 also can be used.

TABLE 2

Combinations of monomers and fluorescent dyes for use in polymeric nanoparticle taggants.

| Monomers | Dyes |
| --- | --- |
| Styrene | Fluorescein isothiocyanate (FITC) |
| Aminostyrene | Solvatochromic Nile red |
| Methoxystyrene | Dipicolinic acid |

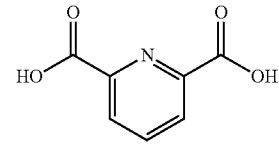

TABLE 2-continued

Combinations of monomers and fluorescent dyes for use in polymeric nanoparticle taggants.

| Monomers | Dyes |
|---|---|
| Bromostyrene | Fluorescein |
| Chlorostyrene | Fluorescein isothiocyanate (FITC) |
| Butylmetacrylate | Rhodamine |
| T-butyoxystyrene | Cyanine-5 |
| Trifluoromethy styrene | 9,10-diphenylanthracene |

In some examples, the fluorescent dye loaded nanoparticle taggants are provided with selective surface functionality. For example, fluorescent dye loaded polymeric nanoparticles can be surface functionalized with glycidylated polyethylenimine to impart colloidal stability in brines. The polymeric nanoparticles can be surface functionalized to reduce retention to reservoir rocks and keep the nanoparticles stable/suspended in the hot briny environment so that the nanoparticles can be transported deep into the reservoir with injected water. Similarly, the wettability of the nanoparticle tags can be tuned by surface functionalization to perform with optimal cuttings penetration in either oil-base or water-base mud systems. For example, a positively charged polyethylenimine coating will have affinity for drill cuttings from siliciclastic reservoirs. Surface functionalization tailoring affinity toward drill cuttings from carbonate reservoirs (for example, coatings with functional groups such as phosphonates and carboxylates) can be engineered as well. The surface of the polymeric nanoparticles may also be selectively hydrophobized for compatibilization with oil-based muds, and impregnation into cuttings with mixed-wettability.

In some examples, the polymeric nanoparticles have ceiling temperatures that do not interfere with pyrograms for source rock decomposition, such as ceiling temperatures between 400° C. and 800° C. For instance, styrenic nanoparticles can have ceiling temperatures between 600° C. and 800° C. and methacrylic nanoparticles can have ceiling temperatures between 400° C. and 800° C. Polymeric nanoparticle taggants with these ceiling temperatures allow both origin depth identification and pyrolysis-GCMS analysis to be performed to determine composition and properties of drill cuttings.

EXAMPLE

Figure 7:
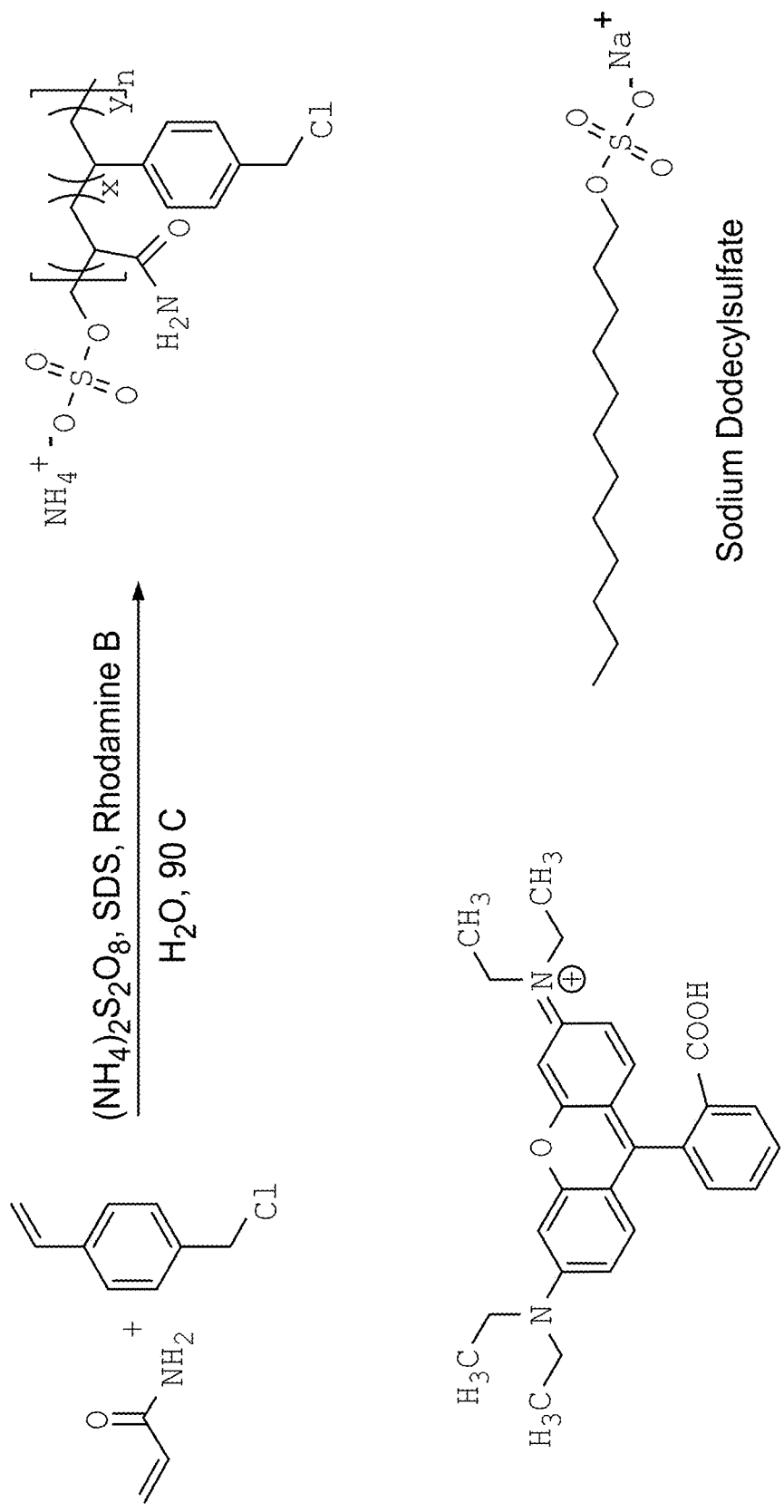
FIG. 7 is a scheme for synthesis of fluorescent dye loaded nanoparticle taggants.

The following description is an example of an emulsion polymerization process for synthesizing polystyrenic nanoparticle taggants loaded with Rhodamine B fluorescent dye according to the synthetic scheme shown in FIG. 7. Two types of nanoparticle taggants were synthesized, "A" and "B," containing different amounts of Rhodamine B. Amounts of starting materials for types A and B are shown in Tables 3 and 4, respectively.

TABLE 3

Raw materials for synthesis of type A nanoparticle taggants.

| Raw materials | density (g/ml) | Mw (g/mol) | concentration (%) | Mass (g) | Mole |
|---|---|---|---|---|---|
| vinyl benzyl chloride | 1.083 | 152.04 | 1.81% | 1 | 0.006577217 |
| Initiator (NH4)2S2O8 | | 228.18 | 0.167% | 0.0925 | 0.000405473 |
| SDS (NaC12H25SO4) | | 288.372 | 0.36% | 0.2 | 0.000693549 |
| Acryamide | | 71.08 | 0.21% | 0.116877138 | 0.001644304 |
| Rhodamine | | 479.02 | | 0.005 | 1.0438E−05 |

TABLE 4

Raw materials for synthesis of type B nanoparticle taggants.

| Raw materials | density (g/ml) | Mw (g/mol) | concentration (%) | Mass (g) | Mole |
|---|---|---|---|---|---|
| vinyl benzyl chloride | 1.083 | 152.04 | 1.81% | 1 | 0.006577 |
| Initiator (NH4)2S2O8 | | 228.18 | 0.167% | 0.0925 | 0.000405 |
| SDS (NaC12H25SO4) | | 288.372 | 0.36% | 0.2 | 0.000694 |
| Rhodamine B | | 479.02 | 0.02% | 0.01 | 2.09E−05 |

Figure 8:
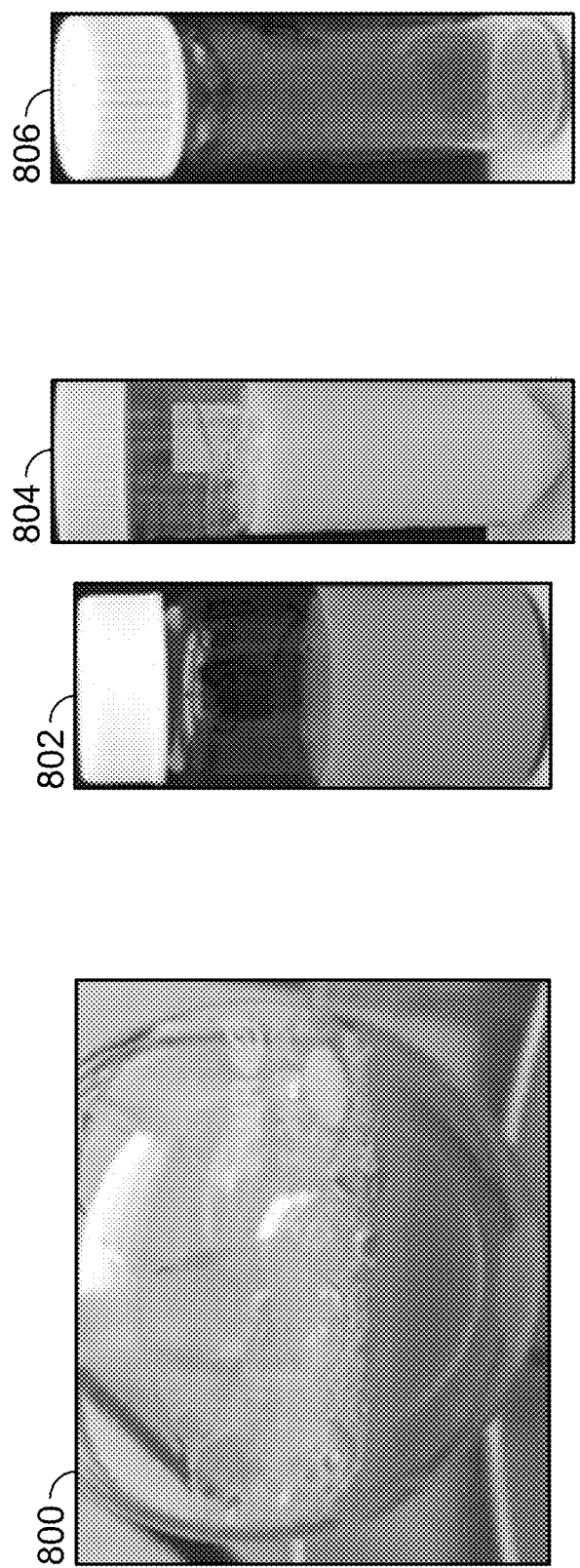
FIG. 8 are photographs of intermediates and products of a synthesis of fluorescent dye loaded nanoparticle taggants.

Referring to FIG. 8, rhodamine B and SDS were dissolved in 55 milliliters (mL) of deionized (DI) water, yielding a red solution 800. The red solution 800 was bubbled under nitrogen gas (N2) for 15 minutes, then heated to 90° C. using an oil bath. Acrylamide, dissolved in 1-2 mL of DI water, was injected into the rhodamine/SDS solution, followed by dropwise injection of vinylbenzene chloride. Dispersions 802, 804 of types A and B, respectively, red poly(vinyl benzyl chloride) nanoparticles loaded with rhodamine B in the red dye solution formed after mixing for 2 hours at 90° C. Dynamic light scattering (DLS) measurement of the dispersion 802 indicated that the particle size of the as-formed nanoparticles A and B was 173.13±1.83 nm and 51.54±1.15 nm, respectively.

The nanoparticles were precipitated out of dispersion by adding an equal volume of methanol to the dispersion, resulting in red solid nanoparticles 806, that were separated from the liquid using centrifugation. The red solid nanoparticles 806 were transferred to a 15 mL centrifuge filter with a 3 k membrane. The red solid nanoparticles 806 was washed three times using DI water and centrifuging at 9000 rpm for 10 minutes. The solid was freeze-dried under vacuum.

Figure 9:
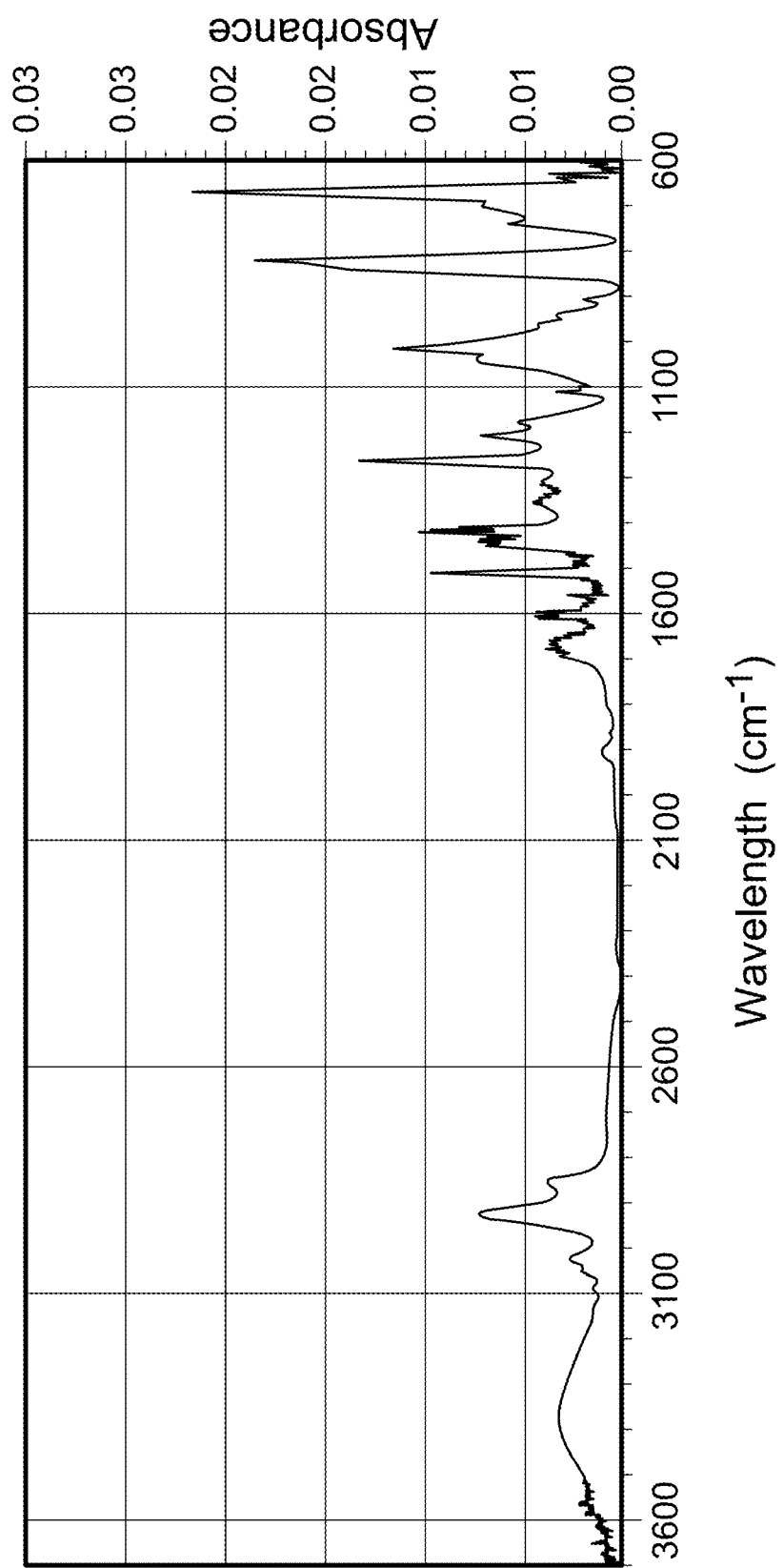
FIG. 9 is a Fourier transform infrared spectrometry-attenuated total reflectance (FTIR-ATR) spectrum of polymeric nanoparticle taggants loaded with Rhodamine B fluorescent dye.

FTIR-ATR (Fourier transform infrared-attenuated total reflectance) data was collected on a Nicolet™ iS50 FTIR Spectrometer (Thermo Scientific) using an ATR module, an ATR iD7/iTX GE crystal, and a DTGS (Deuterated triglycine sulfate) potassium bromide (KBr) detector. The FTIR-ATR spectra were collected using 100 scan averages at a 4 wavenumber (cm$^{-1}$) resolution over a 600-4000 cm$^{-1}$ range. The FTIR-ATR spectrum of the type A nanoparticles is shown in FIG. 9.

Figure 10:
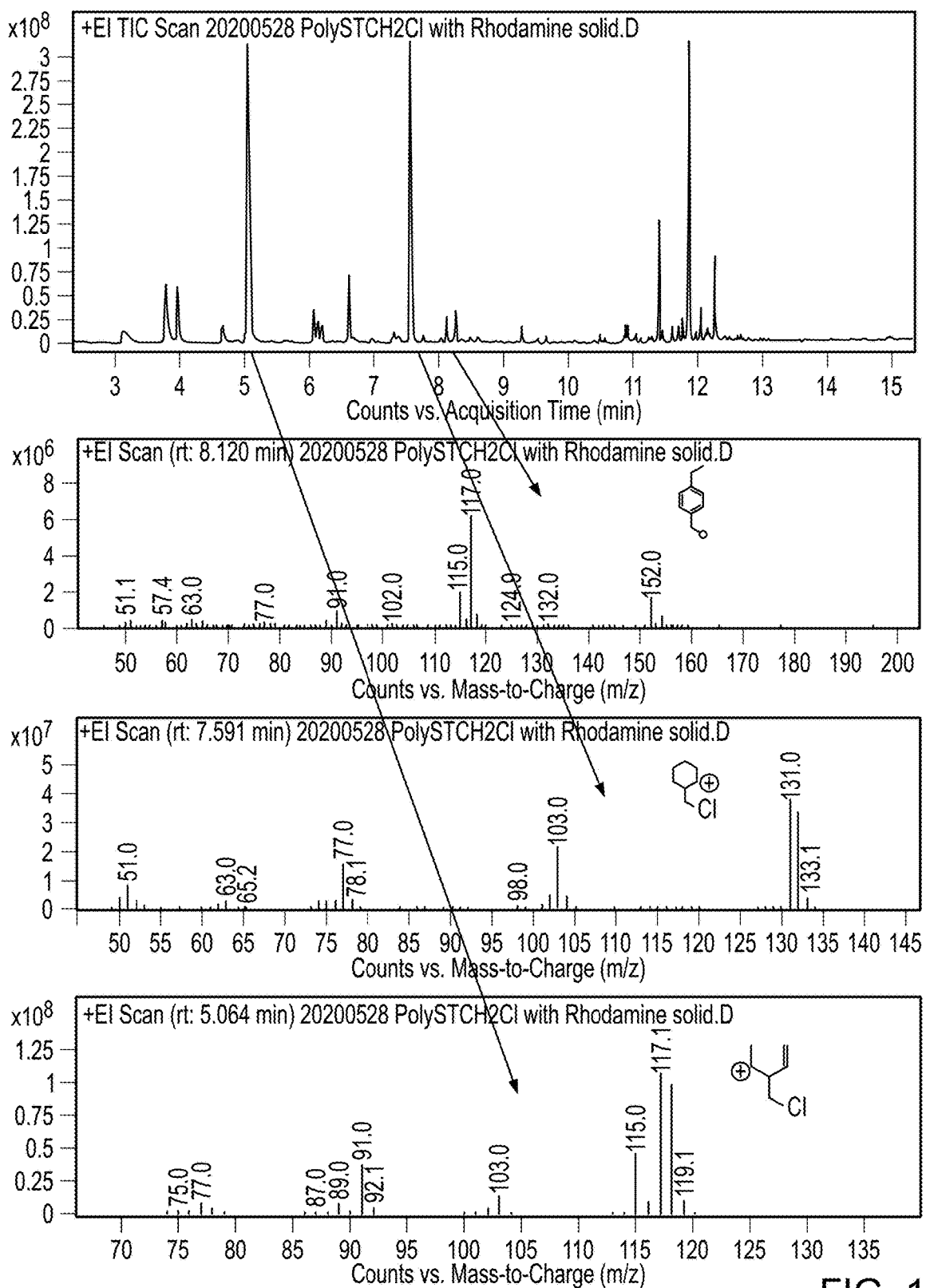
FIG. 10 shows pyrolysis-GCMS (gas chromatography-mass spectrometry) chromatogram and mass spectra of polymeric nanoparticle taggants loaded with Rhodamine B fluorescent dye.

Pyrolysis-GCMS was performed with a Frontier pyrolyzer (Frontier Lab) linked to a GC-MS system (Agilent Technologies), as used for evolved gas analysis (EGA). For these measurements, the nanoparticles were flash pyrolyzed at 550° C. for 0.2 minutes. The column used for separation was an Agilent HP-5 ms ultra inert (UI) column with the following specifications: 30 meter length, 0.25 millimeter (mm) inner diameter (ID), and 0.25 micrometer (m) film. The set temperature of the back inlet was 280° C. with a split ratio of 25 to 1 and a split flow of 25 milliliters per minute (mL/min). The flow rate of the carrier helium gas through the column was 1.1 mL/min at a constant flow mode. The oven temperature started at 75° C. and increased to 150° C. at 10° C. per minute (° C./min), and then to 325° C. at 50° C./min. The pyrolysis-GCMS chromatogram and the mass spectra of the nanoparticles type A are shown in FIG. 10. The m/z of vinylbenzyl chloride and its derivatives are visible on the mass spectra.

Other schemes for attaching fluorescent dyes to polymers can also be used for formation of fluorescent dye loaded polymer taggants.

Figure 11A:
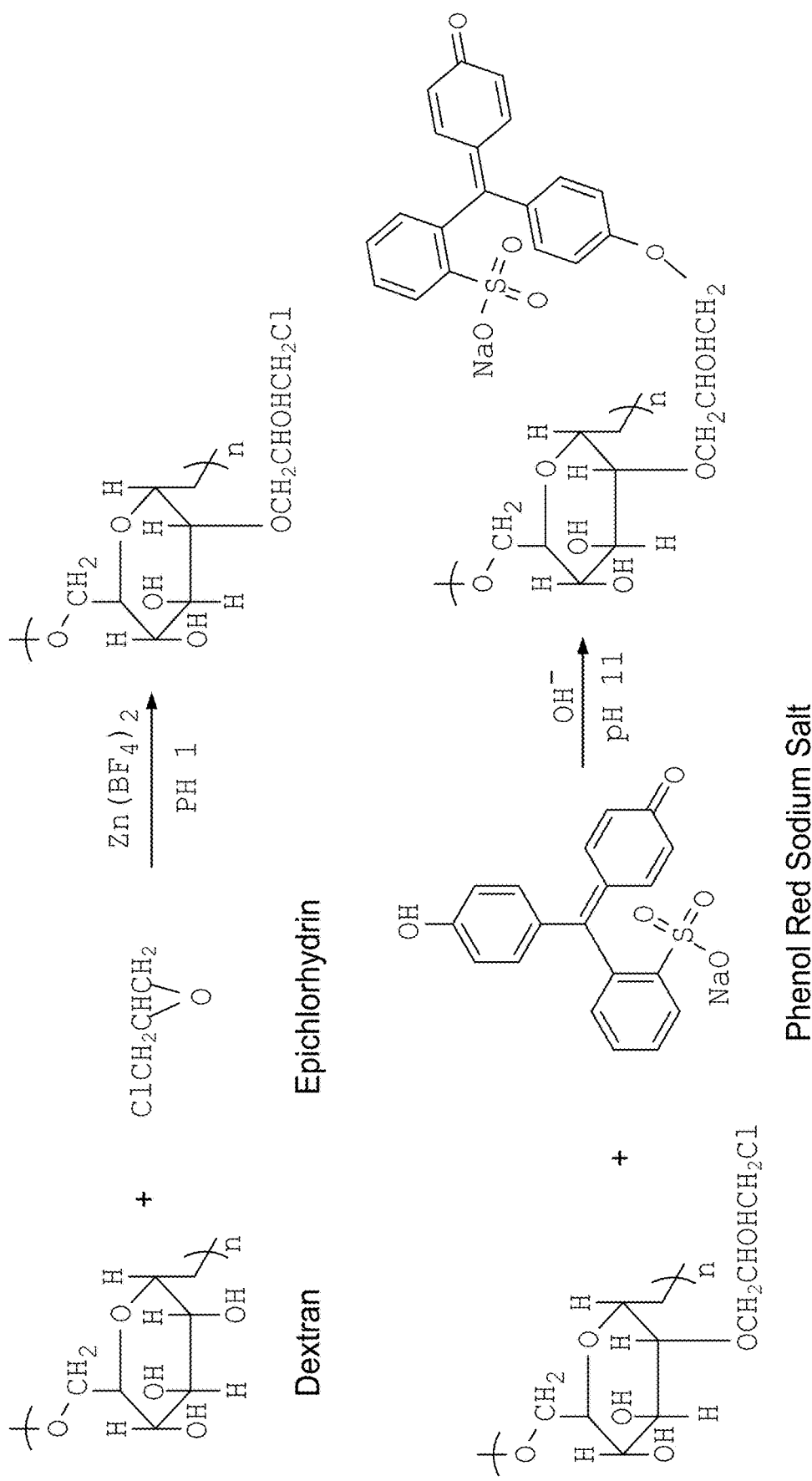
FIG. 11A is a scheme for synthesis of fluorescent dye loaded polymer taggants.
Figure 11B:
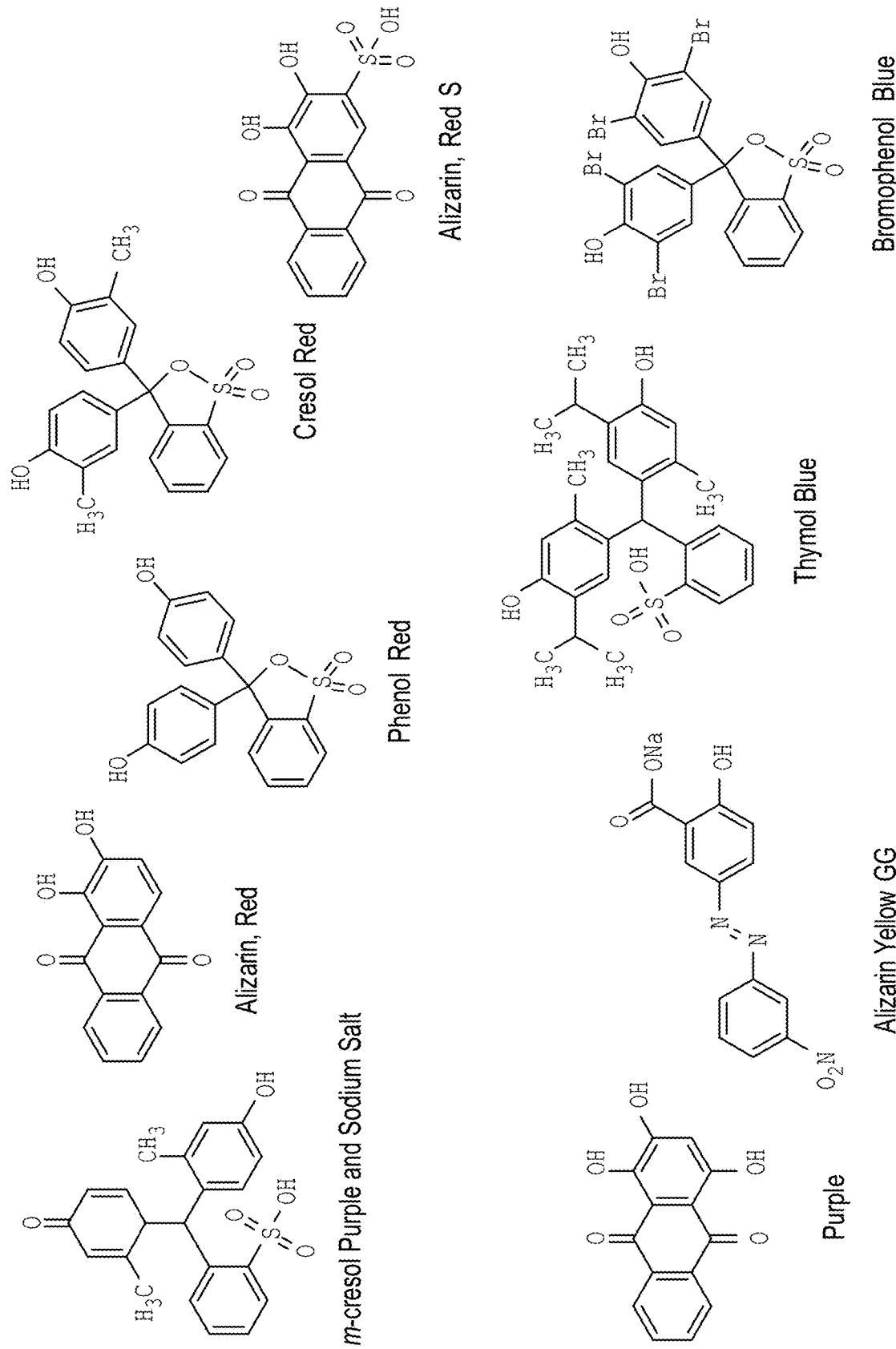
FIG. 11B shows fluorescent dyes.

In some examples, fluorescent dye loaded polymer taggants are formed by reacting polysaccharides with a fluorescent dye. In the specific example of FIG. 11A, phenol red substituted dextran is formed. Dextran is a water soluble polymer with hydroxy groups that react with epichlorhydrin to form a chlorinated derivative. The chlorinated dextran reacts with phenol red solution in water at pH 11 to form phenol red substituted dextran. Other polysaccharides, such as xanthan, cellulose, or starch, can be used in place of dextran in these reactions. Fluorescent dyes other than phenol red also can be used. Examples of suitable fluorescent dyes are shown in FIG. 11B and include m-cresol purple, Alizarin red, Alizarin red S, Alizarin Yellow GG, cresol red, purple, Thymol blue, and bromophenol blue.

Figure 12A:
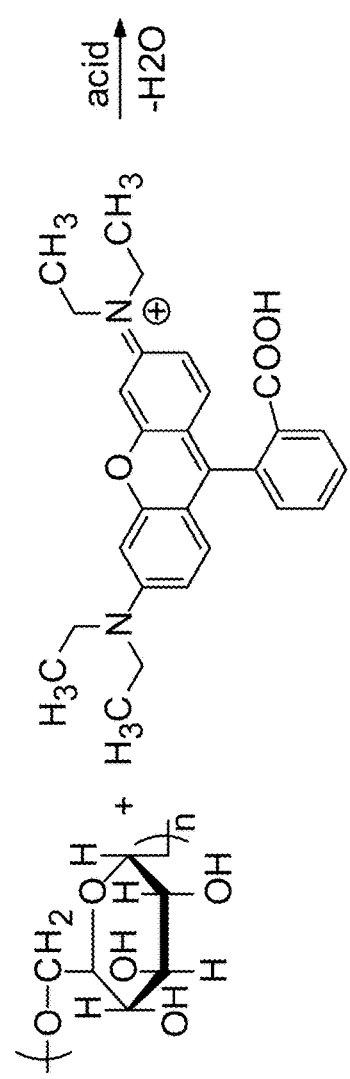
FIG. 12A is a scheme for synthesis of fluorescent dye loaded polymer taggants.
Figure 12A:
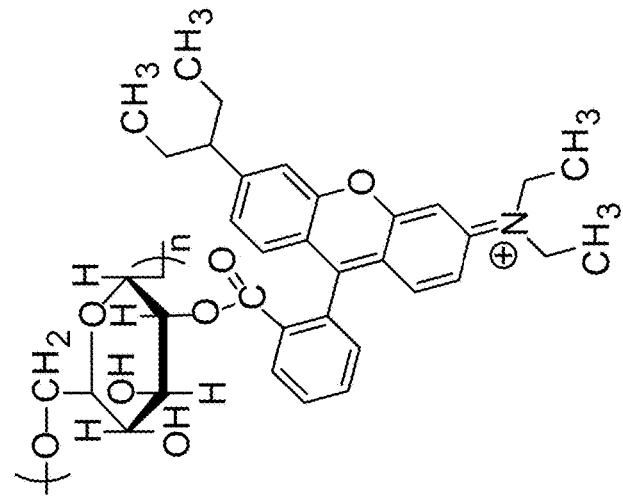
Figure 12B:
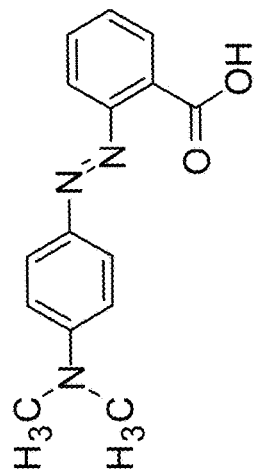
FIG. 12B shows fluorescent dyes.
Figure 12B:
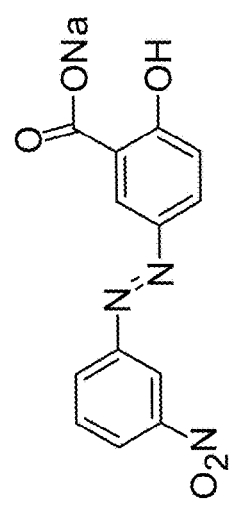
Figure 12B:
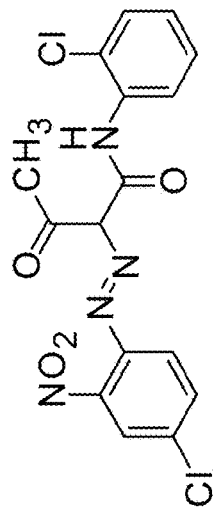

In some examples, fluorescent dye loaded polymer taggants are formed by attaching fluorescent dye to a polysaccharide using a condensation reaction, such as through ester bond formation. In the specific example of FIG. 12A, Rhodamine B is attached to dextran through ester bond formation between the hydroxy groups on dextran and the acid group on Rhodamine B. Fluorescent dyes containing acid or ester groups, such as those shown in FIG. 12B, can be used in place of Rhodamine B in such condensation reactions.

Figure 13:
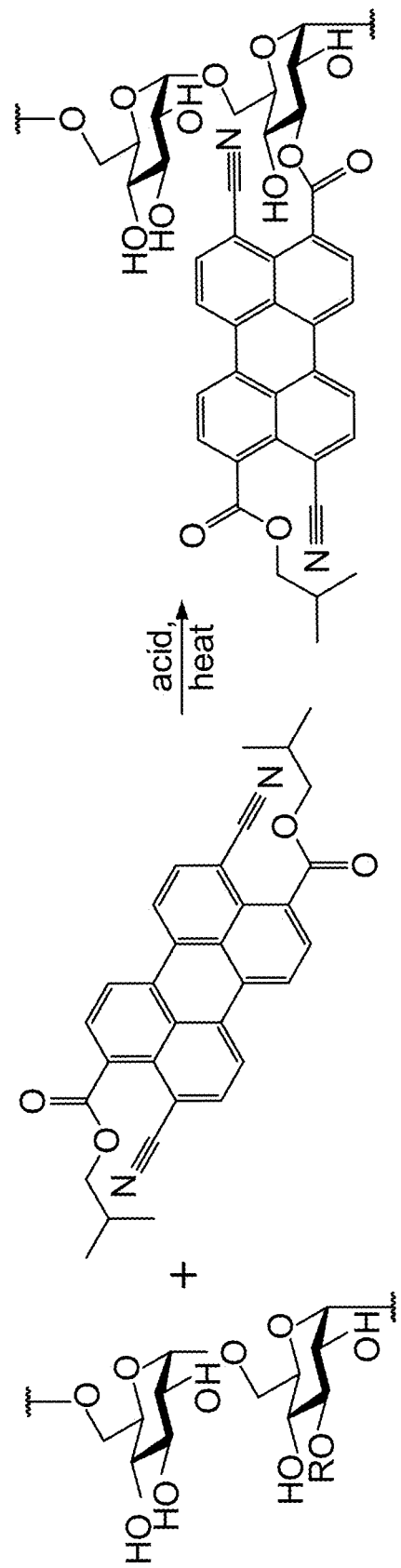
FIG. 13 is a scheme for synthesis of fluorescent dye loaded polymer taggants.

In some examples, fluorescent dye loaded polymer taggants are formed by attaching fluorescent dye to a polysaccharide through a transesterification reaction, in which a dye is linked through ester bond formation between an ester group on the dye and hydroxy groups on the polysaccharide. In the specific example of FIG. 13, dextran is reacted with lumogen yellow 083. Other dyes containing ester groups, such as rhodamine 6G, also can be used in such transesterification reactions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A method of surface logging a well, the method comprising:
    adding each of multiple polymeric taggants to a circulating drilling fluid in an addition sequence while drilling the well, wherein each polymeric taggant comprises a polymer and a respective fluorescent dye, wherein each fluorescent dye has an emission wavelength different from the emission wavelength of each other fluorescent dye, an excitation wavelength different from the excitation wavelength of each other fluorescent dye, or both;
    taking a sample of drill cuttings carried by a drilling fluid while drilling a well in the presence of the drilling fluid, wherein the sample of drill cuttings includes polymeric taggants attached to the drill cuttings;
    extracting the dyes from the sample of drill cuttings into an extract solution;
    determining an indication of the type of and the concentration of each of the dyes in the extract solution; and
    determining a depth associated with the sample of drill cuttings based on the indication of the concentration of each of the dyes and on the addition sequence.

2. The method of claim 1, wherein each polymeric taggant comprises polymeric nanoparticles.

3. The method of claim 1, comprising determining an indication of the type and the concentration of each of the fluorescent dyes in the extract solution based on an excitation spectrum of the extract solution, an emission spectrum of the extract solution, or both.

4. The method of claim 1, wherein determining an indication of the type and the concentration of each of the fluorescent dyes comprises analyzing the extract solution with a fluorimeter or an ultraviolet spectrometer.

5. The method of claim 1, wherein determining an indication of the type and the concentration of each of the fluorescent dyes comprises: illuminating the extract solution; and collecting an emission spectrum from the extract solution responsive to the illumination.

6. The method of claim 5, comprising: determining an intensity of the emission spectrum at the emission wavelength of each of the fluorescent dyes; and determining the indication of the concentration of each of the fluorescent dyes based on the respective intensities.

7. The method of claim 1, comprising determining an indication of the type and the concentration of each of the fluorescent dyes in the extract solution using mass spectrometry.

8. The method of claim 1, comprising determining an indication of the concentration of the polymer of the polymeric taggant in the extract solution using mass spectrometry.

9. The method of claim 1, wherein extracting the fluorescent dyes comprises dissolving the polymer of the polymeric taggant in a solvent.

10. The method of claim 1, wherein the polymer of one or more of the polymeric taggants comprises a styrene based polymer.

11. The method of claim 1, wherein the polymer of one or more of the polymeric taggants comprises a polysaccharide based polymer.

12. The method of claim 1, wherein the polymer of one or more of the polymeric taggants comprises a polymer based on an acrylate, a polyester, a polyamide, or a polycarbonate.

13. The method of claim 1, wherein one or more of the polymeric taggants comprises polymeric nanoparticles with the respective fluorescent dye attached to a polymer of the nanoparticles.

14. The method of claim 1, wherein one or more of the polymeric taggants comprises polymeric nanoparticles with the respective fluorescent dye encapsulated in an interior of the nanoparticles.

15. The method of claim 1, wherein one or more of the polymeric taggants comprises a polymer with the respective fluorescent dye attached to the polymer.

16. The method of claim 1, wherein at least some of the polymeric taggants attach to the drill cuttings during generation of the drill cuttings.

17. The method of claim 1, comprising using pyrolysis-gas chromatography-mass spectrometry to analyze properties of the drill cuttings.

18. The method of claim 1, comprising performing nuclear-based porosity or mineralogy analysis on the drill cuttings.

19. A composition comprising:
drill cuttings obtained from a drilling well; and
one or more polymeric taggants attached to the drill cuttings, wherein each polymeric taggant comprises a polymer and a respective fluorescent dye, and wherein each fluorescent dye has an emission wavelength different from the emission wavelength of each other fluorescent dye, an excitation wavelength different from the excitation wavelength of each other fluorescent dye, or both.

20. The composition of claim 19, wherein the polymer of one or more of the polymeric taggants comprises a styrene based polymer.

21. The composition of claim 19, wherein the polymer of one or more of the polymeric taggants comprises a polysaccharide based polymer.

22. The composition of claim 19, wherein the polymer of one or more of the polymeric taggants comprises a polymer based on an acrylate, a polyester, a polyamide, or a polycarbonate.

23. The composition of claim 19, wherein one or more of the polymeric taggants comprises polymeric nanoparticles with the respective fluorescent dye attached to a polymer of the nanoparticles.

24. The composition of claim 19, wherein one or more of the polymeric taggants comprises polymeric nanoparticles with the respective fluorescent dye encapsulated in an interior of the nanoparticles.

25. The composition of claim 19, wherein one or more of the polymeric taggants comprises a polymer with the respective fluorescent dye attached to the polymer.

26. The composition of claim 19, wherein at least some of the polymeric taggants are adhered to a surface of the drill cuttings.

27. The composition of claim 19, wherein at least some of the polymeric taggants are penetrated within the drill cuttings.

28. The composition of claim 19, wherein the polymeric nanoparticles and fluorescent dyes are soluble in a common organic solvent.

* * * * *